(12) United States Patent
Tombari et al.

(10) Patent No.: US 6,476,223 B2
(45) Date of Patent: Nov. 5, 2002

(54) METHOD FOR OBTAINING N-[3(3-CYANO-PYRAZOLE[1,5-A]PYRIMIDINE-7-YL) PHENYL]-N-ETHYL-ACETAMIDE

(75) Inventors: Dora Tombari; Adriana Vecchioli, both of Buenos Aires (AR)

(73) Assignee: Gador S. A., Buenos Aires (AR)

( * ) Notice: Subject to any disclaimer, the term of this patent is extended or adjusted under 35 U.S.C. 154(b) by 0 days.

(21) Appl. No.: 10/013,762

(22) Filed: Dec. 10, 2001

(65) Prior Publication Data

US 2002/0072605 A1 Jun. 13, 2002

(30) Foreign Application Priority Data

Dec. 13, 2000 (AR) ..................... P 00 01 06596

(51) Int. Cl.$^7$ ............................ C07D 487/04
(52) U.S. Cl. ..................................... 544/281
(58) Field of Search ........................ 544/281

(56) References Cited

U.S. PATENT DOCUMENTS

| 4,626,538 A | 12/1986 | Dusza et al. | 544/281 |
| 5,714,607 A | 2/1998 | Padmanathan | 544/281 |

*Primary Examiner*—John M. Ford
(74) *Attorney, Agent, or Firm*—Notaro & Michalos P.C.

(57) ABSTRACT

An improved method for preparing N-[3(3-cyanopyrazole [1,5-a]pyrimidine-7-yl)phenyl]-N-ethyl-acetamide having the FORMULA I:

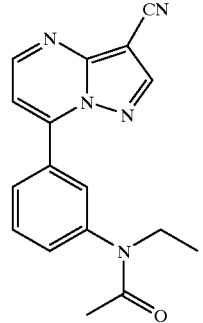

FORMULA I in which the product in question is obtained in "a single step" starting with N-[3-[3-(dimethylamine)-1-oxo-2-propenyl]phenyl]acetamide (II) according to the following sequence:

In a first stage N-[3-[3-(dimethylamine)-oxo-2-propenyl] phenyl]acetamide (II) is added in portions to a suspension of sodium hydride in dimethylformamide in the presence of ethyl iodide. The resulting suspension of compound (III) (N-[3-[3-(dimethylamine)-1-oxo-2-propenyl]phenyl]-N-ethyl-acetamide) is diluted with water until solution A is obtained which is used as it is.

Subsequently, solution A is added to solution B of 3-amino-pyrazole-4-carbonitrile IV) in aqueous DMF/hydrochloric acid.

10 Claims, No Drawings

METHOD FOR OBTAINING N-[3(3-CYANO-PYRAZOLE[1,5-A]PYRIMIDINE-7-YL)PHENYL]-N-ETHYL-ACETAMIDE

FIELD AND BACKGROUND OF THE INVENTION

The present invention relates to an improvement in the method on an industrial scale for the preparation of N-[3(3-cyanopyrazole[1,5-a]pyrimidine-7-yl)phenyl]-N-ethyl-acetamide of FORMULA I.

FORMULA I

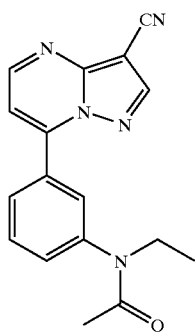

This substance belongs to the group of (7-phenyl)pyrazole-[1,5-a]pyrimidines-(2-amino-disubstituted) which are useful in human medicine as anxiolytic, hypnotic-sedative, and antiepileptic agents as well as skeletal muscle relaxants.

SUMMARY OF THE INVENTION

The present invention involves a simpler method with a higher yield for obtaining the product on an industrial scale, which is the object of the present invention, starting with N-[3-[3-(dimethylamine)-oxo-2-propenyl]phenyl] acetamide (II), in "one step" with a chromatographic purity of 99.5% using HPLC.

The synthesis of this compound has been the object of other patents, such as for example, U.S. Pat. No. 4,626,538 wherein the method for obtaining the product, indicated in DIAGRAM I, is applicable to many compounds of the same family and U.S. Pat. No. 5,714,607, where an improvement of the conditions and the reaction medium of the last step are described, in particular for the compound of the present invention, by the addition of water to the acetic acid, reducing reaction times and temperatures.

DIAGRAM I

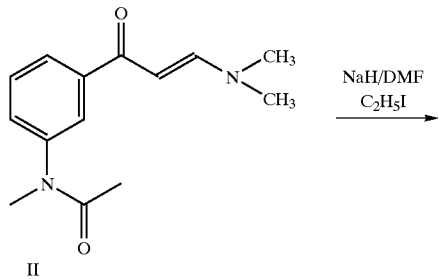

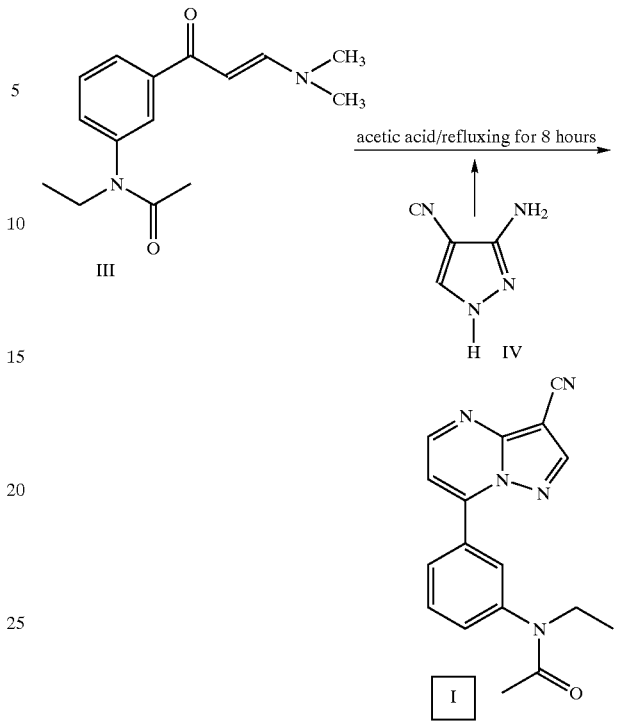

The method, object of the present application, for obtaining the substance of FORMULA I, is a "one step" reaction without isolation of the intermediary (III), (N-[3-[3-(dimethylamine)-1-oxo-2-propenyl]phenyl-N-ethyl-acetamide), generated by the addition in portions of N-[3-[3-(dimethylamine)-1-oxo-2-propenyl]phenyl]acetamide (II) to a suspension of ethyl iodide and sodium hydride (50–60% in mineral oil), using dimethylformamide as a solvent and at a temperature between −15 and 20° C., preferably between −10 and 5° C. The suspension resulting from this synthesis step is diluted with water at a temperature of 0 to 30° C. with the dissolution of the formed compound (III) (N-[3-[3-(dimethylamine)-1-oxo-2-propenyl]phenyl-N-ethyl-acetamide), at a ratio of water/dimethylformamide (DMF) of 0.3–1.5 by volume, preferably at 0.5–0.8 by volume (SOLUTION A).

DIAGRAM II

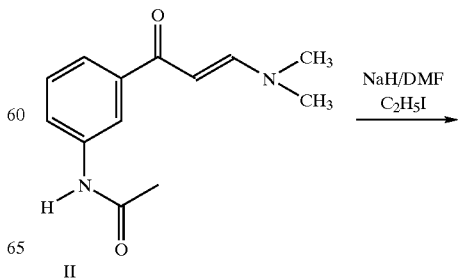

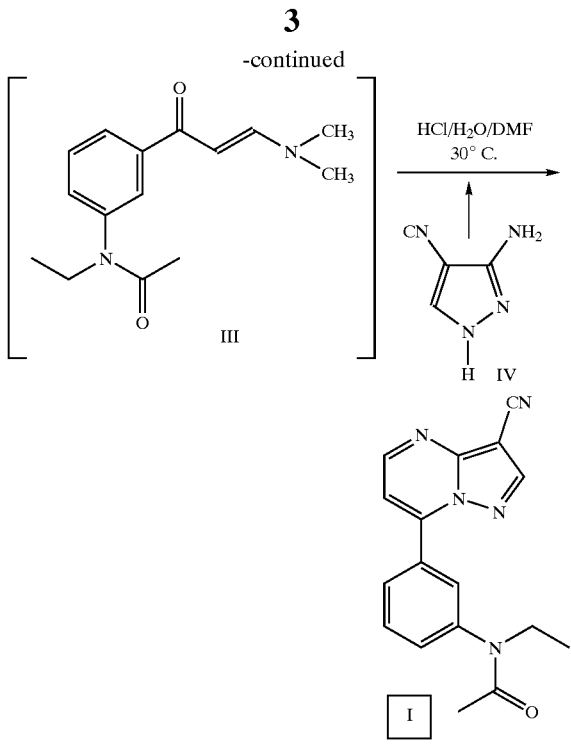

It has been found that the addition of this SOLUTION A to SOLUTION B, which contains the 3-amino-pyrazole-4-carbonitrile (IV) (at a molar ratio of 1 to 2, preferably 1.1–1.5) dissolved in dimethylformamide/hydrochloric acid 2–3 N and (RV: 0.3 to 2.0 by volume) at 20–60° C., preferably at a ratio of volume of DMF/hydrochloric acid 3 N of 0.4–0.7 by volume and at 25–35° C., allows:

- The titration of solution A, which contains compound III, which minimizes the possibility of decomposition of said compound by exposure to the acidic medium.
- The condensation reaction and subsequent cyclization between compounds III and IV to be rapid since it is carried out at a pH lower than 3, preferably lower than 2.
- Obtaining the FORMULA I compound in excellent quality and with a reaction time between 3–5 hours.

From the resulting suspension, or diluted with more water and cooled to a temperature lower than 5° C., a slightly yellowish clear product is obtained with a chromatographic purity by HPLC not less than 99.5% and a global molar yield from both steps of at least 85%, preferably 90% to 95%. The yield obtained when applying the methods described in patents U.S. Pat. No. 4,696,538 and U.S. Pat. No. 5,714,607 are noticeably lower (a difference of approximately 10%) in comparison to the present method.

The color of the crude solids obtained decreases markedly after one recrystallization with solvents such as isopropanol, acetone, 2-butanone, ethyl acetate or methanol. During this process 5–10% by weight of carbon can optionally be used.

Using the method of the present invention, an important advantage lies in achieving a significant shortening of the preparation times by avoiding the isolation of (N-[3-[3-(dimethylamine)-1-oxo-2-propenyl]phenyl]-N-ethyl-acetamide) (III). This is obtained in a dimethylformamide medium and the isolation is complicated and tedious.

By applying the method of the present invention, the quality of this intermediate (determined by HPLC of the solutions) can be expressed as being no less than 94% in area, generally between 95–98%, which is sufficiently pure to ensure the obtainment of the N-[3(3-cyanopyrazole[1,5-a]pyrimidine-7-yl)phenyl]-N-ethyl-acetamide in very good quality.

The yields of these two synthesis steps were not published in U.S. Pat. Nos. 4,626,538 and 5,714,607. However, upon reproducing the samples described in said patents in our laboratory, we have obtained yields markedly lower than those achieved with our "one step" method. These differences in yield are greater than 10% in favor of the present method.

The same were obtained upon reproducing Sample No. 6 of U.S. Pat. No. 4,696,538 in order to obtain N-[3-[3-(dimethylamino)-1-oxo-2-propenyl]phenyl]-N-ethyl-acetamide (III), and sample No. 11 of the method detailed in U.S. Pat. No. 5,714,607 for obtaining N-[3(3-cyanopyrazole[1,5-a]pyrimidine-7-yl)phenyl]-N-ethyl-acetamide (I).

These improvements (fewer number of hours during the preparation and a higher yield), added to the excellent profile of impurities determined by HPLC of the N-[3(3-cyanopyrazole[1,5-a]pyrimidine-7-yl)phenyl]-N-ethyl-acetamide obtained by way of the present method, make this the preferred method for use on an industrial scale. Moreover, the use of the present method ensures a low content of impurities with Rrt (Relative retention time by HPLC) greater than COMPOUND I. We have found that said impurities are difficult to eliminate by conventional purification methods of recrystallization.

The following is a nonlimiting example which illustrates the preparation of N-3(3-cyanopyrazole[1,5-a]pyrimidine-7-yl)phenyl]-N-ethyl-acetamide in a one step synthesis starting with N-[3-[3-(dimethylamine)-oxo-2-propenyl]phenyl] acetamide (II) of excellent quality.

EXAMPLE

Stage 1:

Into a 12-liter reactor, purged and under nitrogen, the sodium hydride is introduced (0.34 kg, 60% in a suspension in mineral oil, 8.5 moles) and dimethylformamide (7.6 liters) followed by cooling to 0–5° C. Ethyl iodide is added (0.605 liters, 7.49 moles), and subsequently N-[3-[3-(dimethylamine)-oxo-2-propenyl]phenyl]acetamide (II) is added in 8–10 portions (1.515 kg, 6.53 moles) maintaining the reaction temperature between −10 and 5° C. The medium is maintained at the same temperature until the end of the reaction (controlled by TLC). Once the reaction is completed, water at −5 and 0° C. (3.53 liters) is added to destroy the excess sodium hydride and to dissolve the (N-[3-[3-(dimethylamine)-1-oxo-2-propenyl]phenyl]-N-ethyl-acetamide) (III) formed. SOLUTION A is obtained.

Stage 2:

3-amino-pyrazole-4-carbonitrile (IV) (0.989 kg, 9.16 moles) in dimethylformamide (3 liters) and hydrochloric acid 3N (5.33 liters) at 50–60° C. is dissolved in a 50-liter reactor. The solution is cooled to 27–32° C. and SOLUTION A (stage 1) is added over 30–60 minutes. The solution maintained at that temperature (27–32° C.) until the reaction is completed (3 to 5 hours) (controlled by HPLC). Water (approximately 9.3 liters) is added to obtain a final ratio of water/DMF of 1.8 by volume. The solution is cooled to 0–5° C. The solid obtained is filtered and washed with water.

Drying takes place at 40–60° C. under an air current. 1.83 kg (92% in moles) is obtained with a purity by HPLC of 99.5% in area.

Recrystallization:

The product can be recrystallized with 2-butanone, among other solvents.

The product obtained in Stage 2 (1.83 kg) is dissolved in 2-butanone (10 liters) while refluxing. The solution is treated with carbon (0.183 kg) and filtered while hot. It is concentrated down to one half the volume at a reduced pressure and subsequently cooled to −5° C. The resulting suspension is filtered and washed with 2-butanone. It is dried at 40–60° C. 1.59 kg (85%) is obtained.

[Yield in Moles (total two stages): 85–90%]

[Yield in Moles (total 2 stages+recrystallization): 75–80%]

What is claimed is:

1. An improved method for preparing N-[3(3-cyanopyrazole[1,5-a]pyrimidine-7-yl)phenyl]-N-ethyl-acetamide with the formula:

FORMULA I

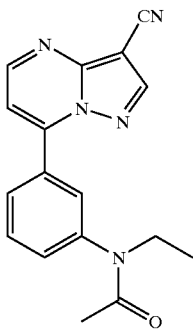

in which the aforementioned product is obtained in "one step", starting with N-[3-[3-(dimethylamine)-1-oxo-2-propenyl]phenyl]acetamide (II), according to the following sequence:

stage 1, in which N-[3-[3-(dimethylamine)-oxo-2-propenyl]phenyl]acetamide (II) reacts with ethyl iodide in the presence of sodium hydride in dimethylformamide. The resulting suspension of compound (III) (N-[3-[3-(dimethylamine)-1-oxo-2-propenyl]phenyl]-N-ethyl-acetamide) is diluted with water until solution A is obtained, which is used as is, stage 2, in which solution A is added to solution B of 3-amino-pyrazole-4-carbonitrile (IV) in DMF/aqueous hydrochloric acid.

2. An improved method as claimed in claim 1, characterized by the addition in portions of N-[3-[3-(dimethylamine)-1-oxo-2-propenyl]phenyl]acetamide (II) to a suspension of ethyl iodide/sodium hydride in dimethylformamide at a reaction temperature between −15 and 20° C., preferably −10 and 5° C.

3. An improved method as claimed in claim 1, characterized by the addition of reactants (addition in portions of compound II to a suspension of sodium hydride and ethyl iodide in DMF) which is inverse in comparison to those known in the art.

4. An improved method as claimed in claim 1, characterized in that there is obtained a solution of compound III in DMF/water, which permits the slow titration of same decreasing the possibility of decomposition of N-(3[3-(dimethylamine)-1-oxo-2-propenyl]phenyl]-N-ethyl-acetamide by exposure to an acidic medium, leading to an excellent grade of purity of the final product.

5. An improved method as claimed in claim 1, characterized in that the ratio of water/DMF in solution A is 0.3 to 1.5, preferably 0.5 to 0.8 by volume.

6. An improved method as claimed in claim 1, characterized by a high purity of compound III in solution A (HPLC: 95–98% in area).

7. An improved method as claimed in claim 1, characterized by the use of hydrochloric acid in solution B.

8. An improved method as claimed in claim 1, characterized in that the reaction temperature of Stage 2 is 20–60° C., preferably 25–35° C.

9. An improved method as claimed in claim 1, characterized in that in Stage 2 the pH is between 1–3, preferably lower than 2.0.

10. An improved method as claimed in claim 1, characterized in that the final ratio of water/DMF is 1.6–2.5, preferably 1.8.

* * * * *